United States Patent [19]

Anderson et al.

[11] Patent Number: 4,636,386

[45] Date of Patent: Jan. 13, 1987

[54] MYCOLOGICAL METHOD FOR CONTROLLING ITALIAN THISTLE GROWTH

[75] Inventors: Gary L. Anderson, Oakland; Steven E. Lindow, Berkeley, both of Calif.

[73] Assignee: The Regents of the University of California, Berkeley, Calif.

[21] Appl. No.: 643,214

[22] Filed: Aug. 22, 1984

[51] Int. Cl.$^4$ .................. A01N 63/00; C12N 1/00; C12R 1/645
[52] U.S. Cl. ........................... 424/93; 435/243; 435/911
[58] Field of Search .................. 435/243, 911; 424/93

[56] References Cited

PUBLICATIONS

ATCC Catalog of Strains I 12th Ed. 1976, pp. 166–168.
Wolf et al., "The Fungi" vol. I p. 170, 1947, (John Wiley and Sons, Pub. London).

*Primary Examiner*—Thomas G. Wiseman
*Assistant Examiner*—Elizabeth C. Weimar
*Attorney, Agent, or Firm*—Bertram I. Rowland

[57] ABSTRACT

A novel pathovar has been isolated and purified, which pathovar most resembles *Alternaria zinniae* Pape, but has a host specificity for Italian thistle. By administering spores of this pathovar, called Alternaria sp., particularly shortly after emergence, Italian thistle growth is substantially inhibited.

The spores of Alternaria sp. described in the subject invention have been deposited at the A.T.C.C. on Aug. 17, 1984 and given Accession No. 20723.

3 Claims, No Drawings

MYCOLOGICAL METHOD FOR CONTROLLING ITALIAN THISTLE GROWTH

BACKGROUND OF THE INVENTION

1. Field of the Invention

There is a continuing need to control weeds which interfere with the growth, maintenance and harvesting of crops. The Italian thistle which is endogenous to the Mediterranean area is now also found in California and environs. The Italian thistle is a major weed pest, occurring in pasture, range land and ruderal areas and is especially a problem in grazing areas where dense stands cause eye injury to cattle. In addition, its presence in orchards or farmland, can interfere with the maintenance and harvesting of crops.

It is therefore desirable to provide an inexpensive, safe and ecologically acceptable way for inhibiting the growth of thistle, without harming other desirable crops or grasses.

2. Description of the Prior Art

Walker and others have reported that *A. macrospora*, *A. cassiae* and *A.* sp. are phytopathogenic to spurred anoda, sicklepod and leafy spurge, respectively. See Walker, *Weed Science* (1981) 29:505-507; Walker, ibid (1981) 29:629-631; and Walker and Riley, ibid (1982) 30:651-654. See also, Krupinsky and Lorenz, ibid (1983) 31:86-88. A method of growing spores is described by Walker, (1980) USDA Science and Education Administration Advanced Agricultural Federal Bulletin Southern Series. ISSN 01923-3728 No. 12.

SUMMARY OF THE INVENTION

A unique pathovar, resembling *Alternaria zinniae* Pape is provided for controlling the growth of Italian thistle (*Carduus pycnocephalus*). The organism, Alternaria sp. is found to have a strong preference for Italian thistle, lacking phytopathogenicity to a large number of other plants. By providing a phytotoxic amount of spores at or about the time of post emergence of Italian thistle, growth of the Italian thistle can be inhibited.

DESCRIPTION OF THE SPECIFIC EMBODIMENTS

An Alternaria sp., which exists in nature, is provided substantially free of other organisms and vegetation for use in the control of Italian thistle (*Carduus pycnocephalus*). The organism based on host specificity is either an aberrant strain or a previously undescribed species. On the basis of conidia morphology and the family of susceptible plants, the fungus most resembles *Alternaria zinniae* Pape. The conidia of the Alternaria sp. were noncatenatae and highly pigmented. The spore body ranges from 40 to 80 $\mu$m in length, from 15 to 25 $\mu$m in width, with 4 to 10 transverse and 0 to 3 longitudinal septa.

The subject fungus can exist in vegetative form or as spores and is most conveniently stored and employed for Italian thistle control as conidia. The fungal spores may be grown by applying the fungus to host leaf tissue in a moist chamber having a relative humidity of at least about 95% for about one day, where the fungus will sporulate on the leaf tissue. The spores may then be transferred to potato dextrose or pea straw agar for multiplication, where growth occurs under alternating dark-light conditions of 12hr periods each. The temperature is about 22° C. during the light cycle and 13° C. during the dark cycle. Desirably, an antibiotic is included in the agar to inhibit bacterial growth, e.g., streptomycin at 25-100 mg/L.

The spores may be formulated in a wide variety of formulations, where the spores will be present in at least about $10^4$ spores/ml and will usually not exceed about $10^7$ spores/ml. Other additives may include surfactants which are nontoxic to plants and are physiologically acceptable. Anionic and nonionic detergents may be employed, generally in amounts of about 0.01-0.1 weight percent. Other additives may also include buffers, other herbicides, sticking agents, and the like. In dry formulations, various additives include inert powders, salts, anti-caking agents, nutrients, buffers, film-forming materials, other herbicides, and the like. The various additives will range in concentration from about $1 \times 10^{-4}$ to 1 weight percent. These formulations are conventional, and need not be extensively exemplified.

The rate of application will vary widely, depending upon whether the formulation is applied directly to the plant or is broadcast over a wide region. For direct application, the solution applied to the plant will be about $10^4$ to $10^7$ spores/ml, while for spraying over a wide area, generally the treatment per hectare will be from about 0.02 to 20 kg of dried organism, preferably 0.1 to 2 kg of dried organism. Application will usually be by spraying to run off, although the formulation can be poured onto the Italian thistle as a liquid or a powder.

The spores should be applied to the Italian thistle before the Italian thistle has reached substantial growth. Generally the spores should be applied at about or prior to the cotyledon stage of growth (first leaf), either pre-emergent or post-emergent, preferably post-emergent. The subject fungus is found to be non-phytopathogenic to members of the families Compositae, Cucurbitaceae, Malvacae, Gramineae, Solanaceae, Umbelliferae, as evidenced by the lack of phytopathogenicity to such crops as potatoes, tomatoes, carrots, safflower and artichokes.

The following description is offered by way of illustration and not by way of limitation.

EXPERIMENTAL

The isolate of Alternaria used in this study was obtained from diseased *C. pycnocephalus* cotyledons in December 1983 collected near Berkeley, Calif. Spores of this fungus were produced by a procedure similar to that of Walker and Riley, (1982) supra. Three liter flasks containing one liter of a culture medium consisting of soybean flour, 15g/L; corn meal, 15 g/L; sucrose, 30 g/L; $CaCO_3$, 3 g/L and distilled water were inoculated with a 1 cm$^2$ section of potato dextrose agar containing mycelium of the fungus and inoculated for 3 to 4 days on a rotary shaker at 24° C. Mycelia were separated from growth medium by filtration and minced for 30 sec in a Waring blender. The mycelial homogenate was poured into 40×60 cm plastic trays to a depth of ca. 0.5 cm and incubated for 2 days at 24° C. with an 11 hr light cycle as described by Walker, (1980) supra. The trays were allowed to air dry in a ventilated chamber for 24 hr. The surface of the mycelial mat was covered with conidiophores and conidia which were harvested with a cyclone spore collector (Tervet and Cherry, *Plant Dis. Rep.* (1950) 34:328) and stored at 5° C. until needed.

Plant inoculation studies

Seeds of *C. pycnocephalus* obtained from Mendocino and Alameda counties of California were planted in 7 cm plastic pots containing UC soil mixtures and were fertilized with half-strength Hoagland solution (Hoagland and Arnon (1950) California Agr. Exp. Sta. Cir. 347 (Revised)). Plants were grown in a glasshouse at 16° C.±2° C. with natural lighting. Plants germinated after ca. 4–7 days; the first true leaf appeared shortly after 2 weeks. After emergence plants were watered once a day at soil level to minimize wetting of the leaves. Seedlings of various stages of growth were inoculated with a spore suspension containing 0.03% Triton CS-7 sticker-spreader in 100 ml distilled water. Spore concentrations were estimated with a hemocytometer. Inoculum was sprayed onto plants with an atomizer until runoff. Inoculated plants were placed in a light-proof moist chamber kept at 95–100% r.h. by two DeVries cold air humidifiers. Unless otherwise stated, plants were kept in the moist chamber for 24 hr at 13° C. and then removed to a glasshouse. Symptoms were observed every day for 14 days.

Identification of causal agents of leaf spotting was obtained by direct observation of sporulation on leaf surfaces of leaves placed in a petri dish lined with filter paper soaked in distilled water to achieve high humidity, and also by placing small surface sterilized leaf segments on potato dextrose agar, and observing the presence of characteristic mycelia or spores produced by Alternaria sp.

Host range study

Non-target weeds and agronomic plants occurring in the same area as *C. pycnocephalus* were inoculated with $10^6$ spores/ml of *Alternaria* sp. as described above. Six pots containing one plant in the cotyledon stage and six pots containing one plant in a mature stage were inoculated. An equal number of uninoculated plants were also used in this study. Non-target plants were examined for symptom development periodically for 28 days. Any necrotic tissue observed was plated on potato dextrose or pea straw agar to determine the presence of Alternaria sp. Each non-target plant was examined on two separate dates.

Determinations of environmental effects on infection

Eight groups of 10 cotyledon stage *C. pycnocephalus* plants were inoculated with $2\times10^5$ spores/ml Alternaria sp., and another group of 10 uninoculated plants were placed in a moist chamber at 13° C. One group of plants was removed from the moist chamber after 0, 1, 4, 8, 12, 16, 24 and 30 hr and was placed in a glasshouse to allow disease development. Plants were rated for disease incidence and percentage of lead area with lesions 2 weeks after treatment using a visual assessment key and a video assessment device as previously described (Lindow and Webb, *Phytopathology* (1983) 73:520–524). This experiment was performed on two separate dates.

Groups of 20 plants in the cotyledon stage of growth were inoculated with a spore suspension containing 0, $2\times10^3$, $1\times10^4$, $1\times10^5$, $1\times10^6$, and $5\times10^6$ spores/ml on two separate dates. The plants were placed in a moist chamber at 5° C. and then transferred to a glasshouse to allow disease development. Leaves were evaluated for area of necrotic lesions 7 and 14 days after inoculation.

This experimental design was repeated at both 13° C. and 20° C.

Effect of host phenology on infection

Ten *C. pycnocephalus* plants in the cotyledon, cotyledon to the first leaf, second leaf, third leaf, and fourth leaf stage of growth were inoculated with $2\times10^5$ spores/ml and placed in a moist chamber for 24 hr at 13° C. with an equal number of uninoculated plants serving as controls. Each treatment was replicated twice. The plants were evaluated for disease incidence and percentage of leaf area with lesions two weeks after inoculation as described above.

Fungal spores typical of Alternaria were profusely produced on diseased leaf material of *C. pycnocephalus* placed in a plastic petri dish with high relative humidity. The conidia and conidiophores were observed directly from lesions or in culture on pea straw or potato dextrose agar. The fungus sporulated readily on pea straw agar, producing septate, hyaline hyphae ca. $7\mu$ wide. Aerial mycelium was cottony, 2–4 mm high, and white to pale gray.

Sporulation occurred rarely on potato dextrose agar. Aerial mycelium was cottony, 3–5 mm high, off-white to pale gray.

On the basis of conidia morphology the fungus would be put in the noncatenatae section of the genus Alternaria. Conidia were formed singly on conidiophores. Secondary conidia appeared only rarely. An abrupt transition from spore body to beak was typical in conidia. The spore body was 40–80$\mu$ long, 15–25$\mu$ wide, and had 4–10 transverse and 0–3 longitudinal septa. The spores are highly pigmented, ranging from brown to dark olive-brown. This fungus most resembles *A. zinniae* Pape based on morphological and cultural characteristics.

Pathogenicity tests

All *C. pycnocephalus* plants in the cotyledon and third true leaf stage inoculated with the fungus developed lesions. The Alternaria sp. used in this study was consistently reisolated from necrotic lesions. None of the uninoculated control plants developed lesions. The presence of infectious Alternaria sp. conidia isolated from the lesion tissue indicated that Alternaria sp. was the causal agent of the disease.

Host range of Alternaria sp.

Lesion development occurred on *Carduus tenuafloris* and *C. pycnocephalus* plants inoculated with Alternaria sp. (Table 1). Plants in the cotyledon stage of growth were severely stunted or killed, while growth of infected mature plants was not significantly affected. Alternaria sp. was isolated in all cases from the lesion areas. Cotyledon stage *Zinnia elangis* plants developed pinpoint lesions following inoculation with $1\times10^6$ conidia/ml but no Alternaria was isolated from these areas. No other plant species developed any leasions after up to 28 days from inoculation.

*A. zinniae* has been reported as a pathogen on zinnia, lettuce and tomato. This isolate of *A. zinniae* does not exhibit this host range. More detailed work is required to determine if this is a strain of *A. zinniae* with an attenuated host range on a previously undescribed species.

Host phenology effects on infection

Susceptibility of *C. pycnocephalus* to Alternaria sp. decreased with increasing stage of plant growth (Table 2). The disease was lethal to plants only in the cotyledon and cotyledon-1 leaf stage of growth. Average leasion area was examined to determine the relative severity of infection caused by the pathogen. The lesions did not expand beyond 1 cm$^2$ on the older leaf tissue and all new growth (exposed to inoculum) was free of infection. Since the plant can recover from even heavy infection if it is not killed it will likely be important to establish high levels of infection by inoculation at the cotyledon stage for adequate control.

Free moisture requirement

A minimum of 4 hr in a saturated atmosphere was required for establishment of the Alternaria infections in the host plant. The severity of infection and subsequent disease symptoms increased with increased free moisture periods for up to 24 hr when all plants were killed when sufficient inoculum was applied. This indicates that while substantial infections could occur following radiative dew periods, dew periods are not sufficient for optimum infection under field conditions and must be supplemented by rainfall.

Interaction between inoculum concentration and temperature at time of inoculation The lesion area on C. pycnocephalus was increased with increasing spore concentrations at all temperatures of inoculation. Decreasing the temperature, however, decreased the number of infections at any given inoculum concentration. All plants in the cotyledon stage of growth were killed following an inoculation with $10^5$ spores/ml at 20° C. (100% lesion area) while equivalent number of plants killed at 13° C. and 5° C. required the application of $10^6$ spores/ml and $5 \times 10^6$ spores/ml, respectively.

The subject fungus provides numerous advantages for the control of Italian thistle. First, it is an endemic pathogen in California and, therefore, part of the ecological system in an area infested with Italian thistle. Large numbers of spores can be produced and stored easily. The organism is highly effective when applied at an early stage of growth and is non-pathogenic on non-target weeds and agronomic crops. The fungus may be readily applied as spores and does not present an environmental hazard.

Although the foregoing invention has been described in some detail by way of illustration and example for purposes of clarity of understanding, it will be obvious that certain changes and modifications may be practiced within the scope of the appended claims.

TABLE 1

| Susceptibility of various plant species to Alternaria sp. in glasshouse[1]. | | |
|---|---|---|
| | 2 wk[2] | 10 wk |
| Compositae | | |
| Italian thistle (Carduus pycnocephalus L.) | +[3] | + |
| Slender thistle (C. tenuafloris Curt.) | + | + |
| Artichoke (Cynara scolymus L.) | − | − |
| Safflower (Carthamus tinctorius L.) | − | − |
| Milk thistle (Silybum mariannum (L.) Gaertn.) | − | − |
| Spring sow thistle (Sonchus asper (L.) Hill) | − | − |
| Lettuce (Lactucca sativa L.) var. "Greatlakes" var. "Parris Island" | − | − |
| Zinnia (Zinnia elegans Jacq.) | ± | − |
| Cucurbitaceae | | |
| Cucumber (Cucumis sativus L.) | − | − |
| Gramineae | | |
| Barnyard grass (Echinochloa crus-galli (L.) Beauv.) | − | − |
| Johnson grass (Sorghum halepense (L.) Pers.) | − | − |
| Wild oats (Auena fatua L.) | − | − |
| Corn (Zea mays L.) | − | − |
| Leguminosae | | |
| Kidney bean (Phaseolus vulgaris L.) | − | − |
| String bean (Phaseolus vulgaris L.) | − | − |
| Soybean (Glycine max (L.) Merr.) | − | − |
| Malvace | | |
| Cotton (Gossyplum hirsutum L.) | − | − |
| Solanaceae | | |
| Potato (Solanum tuberosum L.) | − | − |
| Tomato (Lycopersicon esculentum Mill.) | − | − |
| Tobacco (Micotiana tubacum L.) | − | − |
| Umbelliferae | | |
| Carrot (Daucus carota L. sub. sp. sativus (Hoffm.) Arcang.) | − | − |

[1]Plants inoculated with $1 \times 10^6$ conidia/ml. of Alternaria sp.. Evaluations were made to 28 days after inoculation.
[2]Plants inoculated 2 weeks and 10 weeks after germination.
[3](+) = lesion development from which Alternaria sp. was isolated;
(−) = no symptoms observed;
(±) = pinpoint lesions from which no Alternaria could be isolated.

TABLE 2

The effect of the stage of growth on plant mortality and percent of leaf area with lesions on C. pycnocephalus inoculated with Alternaria sp.[1]

| Growth stage | Plants killed inoc./control | | % Lesion area inoc./control | |
|---|---|---|---|---|
| Cotyledon | 100 | 0 | 100 ± 0[2] | 0 |
| Cotyledon-1 leaf | 85 | 0 | 92.1 ± 6.3 | 0 |
| 1 - leaf | 0 | 0 | 42.8 ± 18.1 | 0 |
| 2 - leaf | 0 | 0 | 19.5 ± 5.6 | 0 |
| 3 - leaf | 0 | 0 | 9.6 ± 2.5 | 0 |
| 4 - leaf | 0 | 0 | 11.9 ± 5.0 | 0 |

[1]Twenty plants of each growth stage were inoculated with $2 \times 10^5$ conidia/ml and incubated at 13° C. with a 24 hr dew period. Plants were evaluated 14 days after inoculation.
[2]Values of the standard error of a treatment mean at p = 0.05.

What is claimed is:

1. A method for inhibiting the growth of Italian thistle which comprises applying to a field containing thistle at about or prior to the cotyledon stage an amount of Alternaria sp. having A.T.C.C. Accession No. 20723 effective to inhibit the growth of the Italian thistle.

2. A method according to claim 1 wherein said Alternaria sp. are present as spores at a concentration in the range from $10^4$ to $10^7$ spores per ml. in an aqueous medium.

3. A method according to claim 2, wherein said aqueous medium contains from about 0.01 to 0.1 percent of a surfactant.

* * * * *